United States Patent
Johnson et al.

(10) Patent No.: US 6,559,139 B1
(45) Date of Patent: May 6, 2003

(54) COMBINATION CHEMOTHERAPY

(75) Inventors: Candace S. Johnson, Pittsburgh, PA (US); Donald L. Trump, Pittsburgh, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 09/544,724

(22) Filed: Apr. 6, 2000

Related U.S. Application Data

(63) Continuation-in-part of application No. 08/921,170, filed on Aug. 29, 1997, now Pat. No. 6,087,350.

(51) Int. Cl.$^7$ .................. A61K 31/59; A61K 31/56; A61K 31/66; A61K 31/335; A61K 31/135
(52) U.S. Cl. .................. 514/168; 514/170; 514/167; 514/449; 514/110; 514/653
(58) Field of Search ................ 514/168, 170, 514/167, 653, 449, 110, 23, 108

(56) References Cited

U.S. PATENT DOCUMENTS

| | | |
|---|---|---|
| 4,717,721 A | 1/1988 | DeLuca et al. |
| 4,804,502 A | 2/1989 | Baggiolini et al. |
| 5,120,722 A | 6/1992 | Baggiolini et al. |
| 5,145,846 A | 9/1992 | Baggiolini et al. |
| 5,547,947 A | 8/1996 | Dore et al. |
| 5,616,571 A | 4/1997 | Daifotis et al. |
| 5,763,429 A | 6/1998 | Bishop et al. |
| 5,795,882 A * | 8/1998 | Bishop et al. ............... 514/170 |
| 5,804,602 A * | 9/1998 | Slusher et al. ............... 514/574 |
| 5,939,456 A | 8/1999 | Perrine |
| 5,972,917 A | 10/1999 | Bishop et al. |
| 6,015,801 A * | 1/2000 | Daifotis et al. ............. 514/108 |
| 6,034,074 A | 3/2000 | Rodriguez et al. |
| 6,071,897 A | 6/2000 | DeLuca et al. |
| 6,087,350 A * | 7/2000 | Johnson et al. ............. 514/168 |
| 6,162,801 A | 12/2000 | Kita et al. |
| 6,242,434 B1 | 6/2001 | Bishop et al. |
| 6,267,985 B1 | 7/2001 | Chen et al. |
| 6,291,443 B1 | 9/2001 | Jimenez et al. |
| 6,294,192 B1 | 9/2001 | Patel et al. |
| 6,358,939 B1 | 3/2002 | Hayes et al. |

FOREIGN PATENT DOCUMENTS

| | | |
|---|---|---|
| WO | WO 93/00079 | 1/1993 |
| WO | WO 98/56387 A | 12/1998 |
| WO | WO 99/16451 A1 | 4/1999 |
| WO | WO 99/49870 | 10/1999 |
| WO | WO 99/56697 A | 11/1999 |

OTHER PUBLICATIONS

"Effects of Vitamin D and a Vitamin D analogue on a Human Squamous Cell Carcinoma Cell Line", Lapco et al., 1998, abstract.*

"Enhancement of 1,25–dihydroxyvitamin D3–mediated antitumor activity with dexamethasone", 1998, J. Natl. Cancer Inst., 90(2), 134–141, abstract.*
Bechtel et al., *Am. J. of Kidney Diseases*, 25, 2, 291–296 (1995).
Majewski et al., *Cancer Letters*, 75, 35–39 (1993).
Majewski et al., *Cancer Letters*, 89, 117–124 (1995).
Zugmaier et al., *British J. of Cancer*, 73, 1341–1346 (1996).
Tsukamoto et al., *Nephron*, 57, 23–28 (1991).
Kyle et al., *Am. Cancer Soc.*, 45, 1669–1674 (1980).
Peng et al., *Mineral and Electrolyete Metabolism*, 23, 13–18 (1997).
Welsh, *Biochem. Cell Biol.*, 72, 537–545 (1994).
Tannock et al., *J. of Clin. Oncol.*, 14 (6), 1756–1764 (1996).
Kantoff et al., *J. of Clin. Oncol.*, 17 (8), 2506–2513 (1999).
Kreis et al., *British J. of Urology*, 79, 196–202 (1997).
Beer et al., *Proc. Am. Assoc. Cancer Res.*, 40, 84–85 (1999).
Johnson et al., *Proc. Am. Soc. Clin. Oncol.*, 17, 215a (1998).
Modzelewski et al., *Proc. Am. Assoc. Cancer Res.*, 40, 580–581 (1999).
Rueger et al., *Proc. Am. Assoc. Cancer Res.*, 40, 162 (1999).
Trump et al., *Proc. Am. Soc. Clin. Oncol.*, 18, 231a (1999).
Moffatt et al., *Clin. Cancer Res.*, 5, 695–703, (1999).
Light et al., *Cancer Res.*, 57, 3759–3764 (1997).
Cho et al., *Cancer Res.*, 51, 2848–2853 (1991).
Wieder et al., *Proc. Am. Soc. Clin. Oncol.*, 17, 107a (1998).
Hershberger et al., *Proc. Am. Assoc. Cancer Res.*, 40, 12 (1999).
Johnson et al., *Proc. Am. Soc. Clin. Oncol.*, 18, 216a (1999).
Elstner et al., *Cancer Res.*, 56, 3570–3576 (1996).
Getzenberg et al., *Urology*, 50 (6), 999–1006 (1997).
"Stedman's Medical Dictionary," p. 1182 (26$^{th}$ Ed. 1995).
Hershberger et al., Abstract No. 78, *Proc. Am. Assoc. Cancer Res.*, 40, 12 (1999).

(List continued on next page.)

*Primary Examiner*—Zohreh Fay
*Assistant Examiner*—Brian-Yong Kwon
(74) *Attorney, Agent, or Firm*—Leydig, Voit & Mayer, Ltd.

(57) ABSTRACT

This invention relates to combination chemotherapy, particularly involving vitamin D or a derivative thereof. In one aspect, the invention provides a method of killing a cell by first administering to the cell vitamin D (or a derivative) and subsequently administering to the cell a cytotoxic agent. Where this strategy is applied to an intact tumor, the present invention provides a method of retarding the growth of the tumor by first administering vitamin D (or a derivative) to the tumor and subsequently administering the cytotoxic agent. A further aspect of the invention concerns a method of treating prostate cancer within a patient by co-administration of vitamin D (or a derivative) and a glucocorticoid to the patient. In yet a further aspect, the invention provides an improved method of treating a patient with vitamin-D involving the adjunctive administration of zoledronate.

36 Claims, No Drawings

OTHER PUBLICATIONS

Koshizuka et al., Database *BIOSIS* (Online), Database Accession No. PREV199800436029, XP002182309, Abstract (1998) & *Int. J. Oncology*, 13 (3), 421–428 (1998).
Light et al., Abstract No. 2105, *Proc. Am. Assoc. Cancer Res.*, 39, 308 (1998).
Yu et al., Abstract No. 1073, *Proc. Am. Assoc. Cancer Res.*, 39, 157 (1998).
Abe et al., *Cancer Res.*, 46, 6316–6321 (1986).
Abe et al., *Endocrinology*, 129 (2), 832–837 (1991).
Abe–Hashimoto et al., *Cancer Res.*, 53, 2534–2537 (1993).
Bilezikian, *The New England Journal of Medicine*, 326(18), 1196–1203 (1992).
Binderup et al., *Biochemical Pharmacology*, 42(8), 1569–1575 (1991).
Binderup et al., in *Vitamin D: Proceedings of the 8th Workshop on Vitamin D, Paris, France* (A. Norman et al., Eds., Walter de Gruyter, Berlin, 1991, p. 192).
Calverley et al., in *Antitumor Steroids* (Blickenstaff, R.T., Ed., Academic Press, Orlando, 1992, pp. 193–270).
Campbell et al., *J. Mol. Endocrinol.*, 19, 15–27 (1997).
Campbell et al., *Journal of the National Cancer Institute*, 89(3), 182–185 (1997).
Cho et al., *Cancer Res.*, 51, 2848–2853 (1991).
Clark et al., *J. Cancer Res. Clin. Oncol.*, 118, 190–194 (1992).
Colston et al., *Endocrinology*, 108(3), 1083–1086 (1981).
Cross et al., *Arch. Pharmacol.*, 347, 105–110 (1993).
DeLuca, *FASEB J.*, 2, 224–236 (1988).
Dilworth et al., *Biochemical Pharmacology*, 47(6), 987–993 (1994).
Eisman et al., *Cancer Res.*, 47, 21–25 (1987).
Eisman et al., *Lancet*, 2, 1335–1336 (1979).
Elstner et al., *Cancer Res.*, 56 (15), 3570–3576 (1996).
Frampton et al., *Cancer Res.*, 43, 4443–4447 (1983).
Hengst et al., *Science*, 271, 1861–1864 (1996).
Honma et al., *Proc. Natl. Acad. Sci. USA*, 80, 201–204 (1983).
Jimenez et al., *Cancer Res.*, 52 (18), 5123–5125 (1992).
Koeffler et al., *Cancer Treatment Rep.*, 69, 1399–1407 (1985).
Liu et al., *Genes and Devel.*, 10, 142–153 (1996).
McCollum et al., *J. Biol. Chem.*, 53, 293–312 (1922).
McElwain et al., *Mol. Cell. Differ.*, 3, 31–50 (1995).
Mellanby et al., *Lancet*, 1, 407–412 (1919).
Miller et al., *Cancer Res.*, 52, 515–520 (1992).
Minghetti et al., *FASEB J.*, 2, 3043–3053 (1988).
Munker et al., *Blood*, 88(6), 2201–2209 (1996).
Munker et al., *J. Clin. Invest.*, 78, 424–430 (1986).
Nishio et al., *Cancer Journal*, 6 (2), 97–101 (1993).
Peleg et al., *Journal of Biological Chemistry*, 270 (18), 10551–10558 (1995).
Raina et al., *Br. J. Cancer*, 63, 4673 (1991).
Revillion et al., *Int. J. Oncol.*, 5 (5), 1131–1136 (1994).
Rigby et al., *J. Immunol.*, 135(4), 2279–2286 (1985).
Russell, *JAMA*, 273(21), 1699–1700 (1995).
Sauders et al., Abstract No. 1949, *Proc. Am. Assoc. Cancer Res.*, 35, 327 (1994).
Saunders et al., Abstract No. 1787, *Proc. Am. Assn. Cancer Res.*, 34, 300 (1993).
Saunders et al., Abstract No. 2641, *Proc. Am. Assoc. Cancer Res.*, 33, 442 (1992).
Saunders et al., *Gynecologic Oncology*, 51, 155–159 (1993).
Smith et al., Abstract 761, *Proc. Am. Assn. Cancer Res.*, 34, 128 (1993).
Studzinski et al., *Critical Reviews in Eukaryotic Gene Expression*, 3(4), 279–312 (1993).
Tanaka et al., *Clinical Orthopaedics and Related Research*, 247, 290–296 (1989).
Tsuchiya et al., *Journal of Orthopaedic Research*, 11(1), 122–130 (1993).
Van Den Bemd et al., *Proc. Natl. Acad. Sci. USA*, 93, 10685–10690 (1996).
Walters, *Endocr. Rev.*, 13, 719–764 (1992).
Wang et al., *Cancer Res.*, 56, 264–267 (1996).
Waxman et al., *Cancer Res.*, 50, 3878–3887 (1990).
Xu et al., *Experimental Cell Research*, 209, 367–374 (1993).
Yu et al., Abstract 1771, *Proc. Am. Assn. Cancer Res.*, 36, 36, 298 (1995).
Zhou et al., *Blood*, 73, 75–82 (1991).

\* cited by examiner

COMBINATION CHEMOTHERAPY

CROSS-REFERENCE TO RELATED APPLICATIONS

This is a continuation-in-part application of U.S. patent application Ser. No. 08/921,170, filed Aug. 29, 1997, which issued on Jul. 11, 2000, as U.S. Pat. No. 6,087,350.

STATEMENT AS TO RIGHTS TO INVENTIONS MADE UNDER FEDERALLY SPONSORED RESEARCH AND DEVELOPMENT

This invention was made with Government support under Grant Number RO1-CA67267 awarded by the National Cancer Institute of the National Institutes of Health. The United States Government may have certain rights in this invention.

BACKGROUND OF THE INVENTION

Combating the growth of neoplastic cells and tumors has been a major focus of biological and medical research. Such research has led to the discovery of novel cytotoxic agents potentially useful in the treatment of neoplastic disease. Examples of cytotoxic agents commonly employed in chemotherapy include anti-metabolic agents interfering with microtubule formation, alkylating agents, platinum-based agents, anthracyclines, antibiotic agents, topoisomerase inhibitors, and other agents.

Aside from merely identifying potential chemotherapeutic agents, cancer research has led to an increased understanding of the mechanisms by which these agents act upon neoplastic cells, as well as on other cells. For example, cholecalciferol (vitamin D) can effect differentiation and reduce proliferation of several cell types cells both in vitro and in vivo. The active metabolite of vitamin D (1,25-dihydroxycholecalciferol (hereinafter "1,25$D_3$")) and analogs (e.g., 1,25-dihydroxy-16-ene-23-yne-cholecalciferol (Ro23-7553), 1,25-dihydroxy-16-ene-23-yne-26,27-hexafluoro-19-nor-cholecalciferol (Ro25-6760), etc.) mediate significant in vitro and in vivo anti-tumor activity by retarding the growth of established tumors and preventing tumor induction (Colston et al., *Lancet*, 1, 188 (1989); Belleli et al., *Carcinogenesis*, 13, 2293 (1992); McElwain et al., *Mol. Cell. Diff.*, 3, 31–50 (1995); Clark et al., *J. Cancer Res. Clin. Oncol.*, 118, 190 (1992); Zhou et al., *Blood*, 74, 82–93 (1989)). In addition to retarding neoplastic growth, 1,25$D_3$ induces a $G_0/G_1$-S phase block in the cell cycle (Godyn et al, *Cell Proliferation*, 27, 37–46 (1994); Rigby et al., *J. Immunol.*, 135, 2279–86 (1985); Elstner et al., *Cancer Res.*, 55, 2822–30 (1995); Wang et al., *Cancer Res.*, 56, 264–67 (1996)). These properties have led to the successful use of 1,25$D_3$ to treat neoplastic tumors (see Cunningham et al., *Br. J. Cancer*, 63, 4673 (1991); Mackie et al., *Lancet*, 342, 172 (1993), Bower et al., *Proc. Am. Assoc. Cancer. Res.*, 32, 1257 (1991)).

In addition to its antineoplastic and cell-cycle blocking effects, 1,25$D_3$ treatment can lead to hypercalcemia. As a result, 1,25$D_3$ is typically administered for therapeutic applications (e.g., metabolic bone disease) at relatively low doses (e.g., about 1 μg/day to about 2 μg/day per patient) long term. To mitigate the effects of hypercalcemia, analogs have been developed which retain antiproliferative activity without inducing hypercalcemia. (See, e.g., Zhou et al, *Blood*, 73, 75 (1991); Binderup et al., *Biochem. Pharmacol.*, 42, 1569 (1991); Binderup et al., page 192 in *Proceedings of the 8th Workshop on Vitamin D, Paris France* (Norman, A. et al., Eds., Walter de Gruyter, Berlin, (1991))). Many of these synthetic analogs are more potent than 1,25$D_3$ in inhibiting neoplastic growth (for a review of many such analogs, see Calverley et al., "Vitamin D" in Antitumor Steroids (Blickenstaff, R. T., Ed., Academic Press, Orlando (1992))).

The platinum-based agents are widely utilized in chemotherapeutic applications. For example, cisplatin kills tumor cells via formation of covalent, cross- or intrastrand DNA adducts (Sherman et al. *Chem. Rev.*, 87, 1153–81 (1987); Chu, *J. Biol. Chem.*, 269, 787–90 (1994)). Treatment with such platinum-based agents thereby leads to the inhibition of DNA synthesis (Howle et al., *Biochem. Pharmacol.*, 19, 2757–62 (1970); Salles et al., *Biochem. Biophys. Res. Commun.*, 112, 555–63 (1983)). Thus, cells actively synthesizing DNA are highly sensitive to cisplatin (Roberts et al., *Prog. Nucl. Acid Res. Mol. Biol.*, 22, 71–133 (1979); Pinto et al., *Proc. Nat. Acad Sci. (Wash.)* 82, 4616–19 (1985)). Such cells generally experience a growth arrest in $G_2$ and eventually undergo apoptosis. This apoptotic effect is observed at drug concentrations insufficient to inhibit DNA synthesis (Sorenson et al, *J. Natl. Cancer Inst.*, 82, 749–55 (1990)), suggesting that platinum agents act on neoplastic cells via multiple mechanisms. Some cells also demonstrate increased platinum sensitivity when in the $G_1$ phase of the cell cycle (Krishnaswamy et al., *Mutation Res.*, 293, 161–72 (1993); Donaldson et al., *Int. J. Cancer*, 57, 847–55 (1994)). Upon release from $G_0/G_1$-S block, such cells remain maximally sensitized through the remainder of the cell cycle.

Other chemotherapeutic agents act by different mechanisms. For example, agents interfering with microtubule formation (e.g., vincristine, vinblastine, paclitaxel, docetaxel, etc.) act against neoplastic cells by interfering with proper formation of the mitotic spindle apparatus (see, e.g., Manfredi et al., *Pharmacol. Ther.*, 25, 83–125 (1984)). Thus, agents interfering with microtubule formation mainly act during the mitotic phase of the cell cycle (Schiff et al., *Proc. Nat. Acad. Sci. U.S.A.*, 77, 1561–65 (1980); Fuchs et al., *Cancer Treat. Rep.*, 62, 1219–22 (1978); Lopes et al., *Cancer Chemother. Pharmacol.*, 32, 235–42 (1993)). Anti-metabolites act on various enzymatic pathways in growing cells. For example, methotrexate (MTX) is a folic acid analog which inhibits dihydrofolate reductase. As a result, it blocks the synthesis of thymidylate and purines required for DNA synthesis. Thus, the primary impact of MTX is in the S phase of the cell cycle, but it can also impact RNA synthesis in $G_1$ and $G_2$ (Olsen, *J. Am. Acad. Dermatol.*, 25, 306–18 (1991)). Of course, other cytotoxic agents can also be employed (e.g., taxanes such as docetaxel (e.g., TAXATERE®)).

Because of the differences in the biological mechanisms of various cytotoxic agents, protocols involving combinations of different cytotoxic agents have been attempted (e.g., Jekunen et al., *Br. J. Cancer*, 69, 299–306 (1994); Yeh et al., *Life Sciences*, 54, 431–35 (1994)). Combination treatment protocols aim to increase the efficacy of cytopathic protocols by using compatible cytotoxic agents. In turn, the possibility that sufficient antineoplastic activity can be achieved from a given combination of cytotoxic agents presents the possibility of reducing the dosage of individual cytotoxic agents to minimize harmful side effects. In part because the various cytotoxic agents act during different phases of the cell cycle, the success of combination protocols frequently depends upon the order of drug application (e.g., Jekunen et al., supra; Studzinski et al., *Cancer Res.*, 51, 3451 (1991)).

There have been attempts to develop combination drug protocols based, in part, on vitamin D and derivatives thereof. For example, the inhibitory effect of the concurrent administration of 1,25D$_3$ and platinum drugs on the growth of neoplastic cells has been studied (Saunders et al., *Gynecol. Oncol.* 51, 155–59 (1993); Cho et al., *Cancer Res.*, 51, 2848–53 (1991)), and similar studies have focused on concurrent combinations of 1,25D$_3$ and other cytotoxic agents (Tanaka et al., *Clin. Orthopaed. Rel. Res.*, 247, 290–96 (1989)). The results of these studies, however, have been less than satisfactory. In particular, the optimal sequence of drug administration has not been achieved. Moreover, the application of these approaches in therapy would require the long-term application of high doses of 1,25D$_3$ in some protocols, which, as mentioned, can precipitate significant side effects. Thus, there remains a need for an improved method of enhancing the efficacy of chemotherapeutic agents, particularly a need for an improved combination therapy, especially involving vitamin D and derivatives thereof.

BRIEF SUMMARY OF THE INVENTION

This invention relates to combination chemotherapy, particularly involving vitamin D or a derivative thereof. In one aspect, the invention provides a method of killing a cell by first administering to the cell vitamin D (or a derivative) and subsequently administering to the cell a cytotoxic agent. Where this strategy is applied to an intact tumor, the present invention provides a method of retarding the growth pf the tumor by first administering vitamin D (or a derivative) to the tumor and subsequently administering the cytotoxic agent. A further aspect of the invention concerns a method of treating prostate cancer within a patient by co-administration of vitamin D (or a derivative) and a glucocorticoid to the patient. In yet a further aspect, the invention provides an improved method of treating a patient with vitamin-D involving the adjunctive administration of zoledronate.

In some applications, the inventive method is a useful therapy, particularly in the treatment of neoplastic or cancerous diseases. In other applications, the present invention provides a tool for further research pertaining to subjects including neoplastic cell growth, the control and regulation of the cell cycle, and the mechanism and efficacy of cytotoxicity and chemotherapy. In this respect, the inventive method is useful for the development of more refined therapies. The invention can best be understood with reference to the following detailed description.

DESCRIPTION OF THE PREFERRED EMBODIMENTS

In one embodiment, the invention provides a method of killing a cell (e.g., a targeted cell) by first administering vitamin D (or a derivative) to the cell and subsequently administering a cytotoxic agent to the cell. Any period of pretreatment can be employed in the inventive method; the exact period of pretreatment will vary depending upon the application for the inventive method. For example, in therapeutic applications, such pretreatment can be for as little as about a day to as long as about 5 days or more; more preferably, the pretreatment period is between about 2 and about 4 days (e.g., about 3 days). Following pretreatment, the inventive method involves administering a cytotoxic agent. However, in a preferred embodiment, a glucocorticoid (e.g., cortisol, dexamethasone, hydrocortisone, methylprednisolone, prednisolone, prednisone, etc.), diphenhydramine, rantidine, antiemetic-ondasteron, or ganistron can be adjunctively administered, and such agents can be administered with vitamin D (or a derivative). The cytotoxic agent can be administered either alone or in combination with continued administration of vitamin D (or a derivative) following pretreatment. While, typically, treatment ceases upon administration of the cytotoxic agent, it can be administered continuously for a period of time (e.g., periodically over several days) as desired.

The cell can be solitary and isolated from other like cells (such as a single cell in culture or a metastatic or disseminated neoplastic cell in vivo), or the cell can be a member of a collection of cells (e.g., within a tumor). Preferably, the cell is a neoplastic cell (e.g., a type of cell exhibiting uncontrolled proliferation, such as cancerous or transformed cells). Neoplastic cells can be isolated (e.g., a single cell in culture or a metastatic or disseminated neoplastic cell in vivo) or present in an agglomeration, either homogeneously or, in heterogeneous combination with other cell types (neoplastic or otherwise) in a tumor or other collection of cells. Where the cell is within a tumor, the present invention provides a method of retarding the growth of the tumor by first administering vitamin D (or a derivative) to the tumor and subsequently administering the cytotoxic agent to the tumor. By virtue of the cytopathic effect on individual cells, the inventive method can reduce or substantially eliminate the number of cells added to the tumor mass over time. Preferably, the inventive method effects a reduction in the number of cells within a tumor, and, most preferably, the method leads to the partial or complete destruction of the tumor (e.g., via killing a portion or substantially all of the cells within the tumor).

Where the cell is associated with a neoplastic disorder within a patient (e.g., a human), the invention provides a method of treating the patient by first administering vitamin D (or a derivative) to the patient and subsequently administering the cytotoxic agent to the patient. This approach is effective in treating mammals bearing intact or disseminated cancer. For example, where the cells are disseminated cells (e.g., metastatic neoplasia), the cytopathic effects of the inventive method can reduce or substantially eliminate the potential for further spread of neoplastic cells throughout the patient, thereby also reducing or minimizing the probability that such cells will proliferate to form novel tumors within the patient. Furthermore, by retarding the growth of tumors including neoplastic cells, the inventive method reduces the likelihood that cells from such tumors will eventually metastasize or disseminate. Of course, when the inventive method achieves actual reduction in tumor size (and especially elimination of the tumor), the method attenuates the pathogenic effects of such tumors within the patient. Another application is in high-dose chemotherapy requiring bone marrow transplant or reconstruction (e.g., to treat leukemic disorders) to reduce the likelihood that neoplastic cells will persist or successfully regrow.

In many instances, the pretreatment of cells or tumors with vitamin D (or a derivative) before treatment with the cytotoxic agent effects an additive and often synergistic degree of cell death. In this context, if the effect of two compounds administered together in vitro (at a given concentration) is greater than the sum of the effects of each compound administered individually (at the same concentration), then the two compounds are considered to act synergistically. Such synergy is often achieved with cytotoxic agents able to act against cells in the $G_0$-$G_1$ phase of the cell cycle, and such cytotoxic agents are preferred for use in the inventive methods. While any such cytotoxic agent can be employed (as discussed herein), preferred cytotoxic agents are platinum-based agents (e.g., cisplatin, carboplatin, etc.). Without being bound by any particular theory, it is believed that the inventive method effects cytotoxicity of neoplastic cells by inducing a $G_0/G_1$-S phase block in the cell cycle, as mentioned herein. The cells are sensitized to cytotoxic agents able to act on cells in such a blocked stage. Alternatively, synchronization of the release of the cells from the block can render them collectively sensitive to the effects of agents acting later in the cell cycle.

As an alternative to vitamin D, any derivative thereof suitable for potentiating the cytotoxic effect of chemotherapeutic agents can by used within the context of the inventive method, many of which are known in the art (see, e.g., Calverley et al., supra). One preferred derivative is its natural metabolite ($1,25D_3$). However, many vitamin D analogs have greater antitumor activity than the native metabolite; thus the vitamin D derivative can be such an analog of $1,25D_3$. Furthermore, where the inventive method is used for therapeutic applications, the derivative can be a nonhypercalcemic analog of $1,25D_3$, as such analogs reduce or substantially eliminate the hypercalcemic side effects of vitamin D-based therapy. For example, the analog can be Ro23-7553, Ro24-5531, or another analog. In some embodiments, other agents that attenuate (e.g., deactivate) MAP kinase, specifically by inducing MAPK phosphatase, can be used as equivalents of vitamin D (or a derivative).

Pursuant the inventive method, the vitamin D (or a derivative) can be provided to the cells or tumors in any suitable manner, which will, of course, depend upon the desired application for the inventive method. Thus, for example, for in vitro applications, vitamin D (or a derivative) can be added to the culture medium (e.g., mixed initially with the medium or added over time). For in vivo applications, vitamin D (or a derivative) can be mixed into an appropriate vehicle for delivery to the cell or tumor. Thus, for systemic delivery, vitamin D (or a derivative) can be supplied by subcutaneous injection, intravenously, orally, or by other suitable means. Of course, vitamin D (or a derivative) can be provided more directly to the tumor (e.g., by application of a salve or cream comprising vitamin D (or a derivative) to a tumor, by injection of a solution comprising vitamin D (or a derivative) into a tumor, etc.).

The dose of vitamin D (or a derivative) provided to the cells can vary depending upon the desired application. In research, for example, the dose can vary considerably, as dose-response analysis might be a parameter in a given study. For therapeutic applications, because the pretreatment period can be quite brief in comparison with standard vitamin D-based therapies, higher than typical doses (as discussed above) of vitamin D (or a derivative) can be employed in the inventive method without a substantial risk of hypercalcemia. Thus, for example, in a human patient, as little as 1 $\mu$g/day of vitamin D (or a derivative) (which as mentioned above, is within the normal dosage for $1,25D_3$) can be supplied to a patient undergoing treatment, while the maximal amount can be as high as about 20 $\mu$g/day (or even higher in some larger patients). Preferably, between about 4 $\mu$g/day and about 15 $\mu$g/day (e.g., between about 7 $\mu$g/day and about 12 $\mu$g/day) of vitamin D (or a derivative) is delivered to the patient. Typically, the amount of vitamin D (or a derivative) supplied will not be so great as to pose a significant risk of inducing hypercalcemia or provoking other toxic side effects. Hence, where non-hypercalcemic vitamin D derivatives are used, higher amounts still can be employed. Thus, 30 $\mu$g/day or more (e.g., about 40 $\mu$g/day or even 50 $\mu$g/day or more) non-hypercalcemic vitamin D derivative can be delivered to a human patient during pretreatment in accordance with the inventive method. Of course, the desired dose of vitamin D (or a derivative) will depend upon the size of the patient and the mode and timing of delivery. Vitamin D (or a derivative) can be delivered once a day, or several times a day, as desired, or it can be delivered discontinuously (e.g., every other day, or every third day). The determination of such doses and schedules is well within the ordinary skill in the art.

Any cytotoxic agent can be employed in the context of the invention: as mentioned, many cytotoxic agents suitable for chemotherapy are known in the art. Such an agent can be, for example, any compound mediating cell death by any mechanism including, but not limited to, inhibition of metabolism or DNA synthesis, interference with cytoskeletal organization, destabilization or chemical modification of DNA, apoptosis, etc. For example, the cytotoxic agent can be an antimetabolite (e.g., 5-flourouricil (5-FU), methotrexate (MTX), fludarabine, etc.), an anti-microtubule agent (e.g., vincristine, vinblastine, taxanes (such as paclitaxel and docetaxel), etc.), an alkylating agent (e.g., cyclophasphamide, melphalan, bischloroethylnitrosurea (BCNU), etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, camptothecins, etc.), or other cytotoxic agents (e.g., dexamethasone). The choice of cytotoxic agent depends upon the application of the inventive method. For research, any potential cytotoxic agent (even a novel cytotoxic agent) can be employed to study the effect of the toxin on cells or tumors pretreated with vitamin D (or a derivative). For therapeutic applications, the selection of a suitable cytotoxic agent will often depend upon parameters unique to a patient; however, selecting a regimen of cytotoxins for a given chemotherapeutic protocol is within the skill of the art.

For in vivo application, the appropriate dose of a given cytotoxic agent depends on the agent and its formulation, and it is well within the ordinary skill of the art to optimize dosage and formulation for a given patient. Thus, for example, such agents can be formulated for administration via oral, subcutaneous, parenteral, submucosal, intraveneous, or other suitable routes using standard methods of formulation. For example, carboplatin can be administered at daily dosages calculated to achieve an AUC ("area under the curve") of from about 4 to about 15 (such as from about 5 to about 12), or even from about 6 to about 10. Typically, AUC is calculated using the Calvert formula, based on the glomerular filtration rate of creatinine (e.g., assessed by analyzing a plasma sample) (see, e.g., Martino et al., *Anticancer Res.*, 19(6C), 5587–91 (1999)). Paclitaxel can be employed at concentrations ranging from about 50 mg/m$^2$ to about 100 mg/m$^2$ (e.g., about 80 mg/m$^2$). Where dexamethasone is employed, it can be used within patients at doses ranging between about 1 mg to about 10 mg (e.g., from about 2 mg to about 8 mg), and more particularly from about 4 mg to about 6 mg, particularly where the patient is human.

Another embodiment of the invention provides a method of treating prostate cancer within a patient by adjunctively administrating vitamin D (or a derivative) and a glucocorticoid to the patient. Any vitamin D derivative and glucocorticoid can be employed in accordance with this aspect of the invention, many of which are discussed elsewhere herein and others are generally known in the art. Moreover, vitamin D (or a derivative) and the glucocorticoid are delivered to the patient by any appropriate method, some of which are set forth herein. Thus, they can be formulated into suitable preparations and delivered subcutaneously, intravenously, orally, etc., as appropriate. Also, for example, the glucocorticoid is administered to the patient concurrently, prior to, or following the administration of vitamin D (or a derivative). One effective dosing schedule is to delver between about 8 µg and about 12 µg vitamin D (or a derivative) daily on alternative days (e.g., between 2 and 4 days a week, such as Mon-Wed-Fri or Tues-Thus-Sat, etc.), and also between about 1 mg and 10 mg dexamethasone (e.g., about 5 mg) to a human patient also on alternative days. In such a regimen, the alternative days on which vitamin D (or a derivative) and on which the glucocorticoid are administered can be different, although preferably they are administered on the same days. Even more preferably, the glucocorticoid is administered once, by itself, prior to concurrent treatment. Of course, the treatment can continue for any desirable length of time, and it can be repeated, as appropriate to achieve the desired end results. Such results can include the attenuation of the progression of the prostate cancer, shrinkage of such tumors, or, desirably, remission of all symptoms. However, any degree of effect is considered a successful application of this method. A convenient method of assessing the efficacy of the method is to note the change in the concentration of prostate-specific antigen (PSA) within a patient. Typically, such a response is gauged by measuring the PSA levels over a period of time of about 6 weeks. Desirably, the method results in at least about a 50% decrease in PSA levels after 6 weeks of application, and more desirably at least about 80% reduction in PSA. Of course, the most desirable outcome is for the PSA levels to decrease to about normal levels (e.g., less than about 4 ng/ml for at least three successive measurements in a non-prostatectomized individual or less than about 0.2 ng/ml in a prostatectomized individual).

In all aspects of the invention that involve in vivo application, preferably the method is employed to minimize the hypercalcemic properties of vitamin D. One manner of accomplishing this is to employ a nonhypercalcemic analog, such as those discussed above. Alternatively, or in conjunction with the use of such analogs, an agent that mitigates hypercalcemia can be adjunctively delivered to the patient. While any such agent can be employed, bisphosphonates (e.g., alendronate, clodronate, etidronate, ibandronate, pamidronate, risedronate, tiludronate, zoledronate, etc.) are preferred agents for adjunctive administration. Such agents can be administered in any suitable manner to mitigate hypercalcemia. Thus, they can be formulated into suitable preparations and delivered subcutaneously, intravenously, orally, etc., as appropriate. Also, such agents can be administered concurrently, prior to, or subsequent to vitamin D (or a derivative). The dosage of such agents will, of course, vary with the potency of the compounds and also to mitigate any unwanted side effects. Thus, for example, for administration to human patients, the dosage of bisphosphonatescan vary between about 1 mg/day and 500 mg/day (e.g., between about 5 mg/day and 100 mg/day), such as between about 10 mg/day and about 50 mg/day, or even between about 30 mg/day and about 40 mg day, depending on the potency of the bisphosphonates. Generally, it is preferred to employ a more potent bisphosphonate, as less of the agent need be employed to achieve the antihypercalcemic effects. Thus, a most preferred bisphosphonate is zoledronate, as it is effective even at very low doses (e.g., between about 0.5 mg day and about 2 mg/day in human patients, or between about 5 µg/kg to about 25 µg/kg body weight).

Indeed, in another aspect, the invention provides an improved method of employing vitamin D (or a derivative) therapeutically by adjunctively administering zoledronate. The zoledronate can be delivered as an adjunct in conjunction with any protocol in which vitamin D (or a derivative) is employed, such as those discussed herein or otherwise employed. As an adjunct, the zoledronate can be delivered in any desired regimen (several times a day, daily, weekly, etc.), as desired. Preferably, the zoledronate is delivered as a pretreatment, e.g., several hours to several days before treatment with vitamin D (or a derivative) commences. More preferably, the zolendronate is adjunctively administered in an amount sufficient to mitigate the antihypercalcemic effects of vitamin D (or a derivative).

EXAMPLES

While one of skill in the art is fully able to practice the instant invention upon reading the foregoing detailed description, the following examples will help elucidate some of its features. Of course, as these examples are presented for purely illustrative purposes, they should not be used to construe the scope of the invention in a limited manner, but rather should be seen as expanding upon the foregoing description of the invention as a whole.

Example 1

This example explains the materials and general methods employed in the following examples.

Inbred female C3H/HeJ mice age 6–10 weeks were obtained from Jackson Laboratories. The mice were virus antibody-free, age and weight-matched for experimental use, and fed a balanced rodent diet.

SCCVII/SF cells—a murine, rapidly growing, non-metastasizing squamous tumor line—were maintained in vivo in C3H/HeJ mice as described previously (McElwain et al., *Mol. Cell. Diff.*, 3, 31–50 (1995)) by s.c. inoculation of $5\times10^5$ log-phase tissue culture cells in the right flank of the animal. The SCCVII/SF cell line was maintained in vitro in RPMI-1640 supplemented with 12.5% inactivated fetal calf serum (FCS) and 1% penicillin-streptomycin sulfate.

$1,25D_3$ and its non-hypercalcemic analog, Ro23-7553, were initially stored in pure powder form in a sealed light-protective vessel at 4° C. For use, each drug was reconstituted in 100% ethyl alcohol and maintained as described (McElwain et al., *Mol. Cell. Diff*, 3, 31–50 (1995)). The cytotoxic agents (carboplatin, cisplatin, and paclitaxel) were diluted in 0.9% saline and were injected i.p. at various doses in a total volume of 0.2 ml, during the experimental protocols.

The in vitro cytotoxicity of drug on tumor cells was determined via the in vitro clonogenic assay (McElwain et al., *Mol. Cell. Diff.*, 3, 31–50 (1995)) with minor modifications as described herein. Briefly, murine SCCVII/SF cells were pre-treated with either 2 nM or 4 nM $1,25D_3$ or Ro23-7553. While $1,25D_3$ or Ro23-7553 are not stable for long periods in tissue culture media, anti-proliferative effects are observed at 24 hr, 48 hr and 7 day incubation times (McElwain et al., supra). After 48 hours incubation with $1,25D_3$ or Ro23-7553, cells were treated for 2 hours with varying concentrations of cytotoxic agent, washed with RPMI 1640 plus FCS, and plated in various dilutions in 6-well tissue culture plates. Following a 7 day incubation at 37° C. in 5% $CO_2$, monolayers were washed with saline, fixed with 100% methanol, and stained with 10% Giemsa; colonies were counted under light microscopy. The surviving fraction was calculated by dividing the cloning efficiency of treated cells by the cloning efficiency of untreated controls.

The effect of $1,25D_3$ or Ro23-7553 alone and/or in combination with various cytotoxic agents on tumor cells in vivo was determined by a modification of the in vivo excision clonogenic tumor cell survival assay (Johnson et al., *Cancer Chemother. Pharmacol.*, 32, 339–46 (1993)). Briefly, SCCVII/SF tumor bearing animals at 14 days post implantation were treated i.p. for 3 days with 1,25D$_3$ or Ro23-7553 at either 0.5 mg/kg body weight/day or at varying doses of 0.03125–0.5 mg/kg body weight/day. On day 3, animals also received an i.p. dose of either 6 mg/kg body weight or varying doses of 1–6 mg/kg body weight of cytotoxic agent. After 24 hours, aliquots of minced tumor were enzymatically dissociated for 60 min at room temperature with a mixture of type I collagenase (37.5 mg/ml), DNAse (55 mg/ml) and EDTA (1%). Viable tumor cells (determined by trypan blue staining) were then plated at various dilutions. After 7 days incubation, colonies were counted, and numbers of clonogenic cells per gram of tumor were counted. The mean±standard deviation (SD) cell yield, cloning efficiency, and number of clonogenic cells for control (no treatment) tumors (n=40) averaged 139.4±38.2×10$^6$ viable tumor cells/g tumor, 27.0±0.56%, and 37.5±13.3×10$^6$ clonogenic tumor cells/g tumor, respectively. The surviving fraction per gram of tumor is defined as the number of clonogenic tumor cells per gram of treated tumor divided by the number of clonogenic tumor cells per gram of control (untreated) tumor. This assay is an accurate measure of in vivo anti-tumor activity; a surviving fraction less than 0.1 correlates with an actual decrease in tumor volume and an increase in tumor regrowth delay (Braunschweiger et al., *Cancer Res.*, 48, 6011–16 (1988); Braunschweiger et al., *Cancer Res.*, 51, 5454–60 (1991)).

The effect of 1,25D$_3$ or Ro23-7553 alone and/or in combination with various cytotoxic agents on tumor cells in vivo was further assayed by measuring the delay of tumor growth (tumor regrowth assay). SCCVII/SF tumor cells (5×10$^5$) were inoculated s.c. into the flank of the leg of C3H/HeJ mice. On day 9 post implantation, as the tumors were palpable (approximately 5×5 mm), animals were randomized for treatment with low dose i.p. Ro23-7553 (0.214 µg/kg body weight/day) or 1,25D$_3$ (0.2 µg/mouse) using a micro-osmotic pump for continuous delivery over seven days. After 7 days, 6 mg/kg body weight cytotoxic agent was injected i.p. Control animals received either treatment alone or no treatment. Control (no treatment) animals were given injection of vehicle (PBS) alone or sham pumps were implanted. Tumor growth was assessed by measuring the tumor diameter with calipers three times weekly. Tumor volumes were calculated by the formula: volume=length×(width$^2$)/2. Post-treatment volumes were expressed as a fraction of pretreatment volume at the time of initial treatment. Tumor regrowth delay was calculated as the mean±standard deviation of the difference in time for treated and control tumor volumes to reach 4 times the pretreatment volume.

Example 2

This example demonstrates the potential for sensitizing tumor cells to the effects of conventional cytotoxic cisplatin therapy by pretreatment with a vitamin D derivative.

Between 0.2 µg/ml and 0.8 µg/ml cisplatin and Ro23-7553 were tested alone and in combination using the in vitro clonogenic assay for the SCCVII/SF tumor cell line as described above. It was observed that pretreatment of cells with both 2 nM and 4 nM Ro23-7553 significantly enhanced clonogenic cell kill when compared to cisplatin alone or in concurrent administration (i.e., no pretreatment) of cisplatin in combination with Ro23-7553 (p<0.001 ANOVA). Significant enhancement of cisplatin-mediated cytotoxicity was observed even at low doses of cisplatin.

Example 3

This example demonstrates the enhancement of in vivo cisplatin-mediated anti-tumor activity by pretreatment with a vitamin D derivative.

The excision clonogenic kill assay was employed wherein SCCVII/SF tumor bearing animals at 14 days post implantation were treated i.p. for 3 days with 0.5 mg/kg body weight/day of Ro23-7553. On the third day animals received varying doses of cisplatin. After 24 hours, tumors were harvested, dissociated, and plated for a 7 day incubation. It was observed that pretreatment for 3 days with the Ro23-7553 before cisplatin resulted in a significant enhancement of clonogenic cell kill when compared to animals treated with cisplatin or Ro23-7553 alone (p<0.001 ANOVA). A significant increase in clonogenic tumor cell kill was observed at each cisplatin dose tested as compared to cisplatin alone.

To determine the effect of varying the Ro23-7553 dose in this assay, SCC tumor-bearing mice were treated daily for 3 days with from 0.03125 mg/kg body weight/day to 0.5 mg/kg body weight/day Ro23-7553. On day 3, cisplatin was administered at 6 mg/kg body weight. It was observed that Ro23-7553 was capable of significantly enhancing cisplatin-mediated tumor cell kill even at the lowest doses tested as compared to cisplatin or Ro23-7553 alone (p<0.01 ANOVA). No animals in either experimental approach became hypercalcemic at any of the Ro23-7553 doses.

Example 4

This example demonstrates the enhancement of in vivo displatin-mediated anti-tumor activity by pretreatment with a vitamin D derivative.

The tumor regrowth assay was employed wherein SCCVII/SF tumor-bearing mice (day 9 post implantation) were treated with Ro23-7553 administered continuously. At the end of Ro23-7553 administration. cisplatin was injected i.p. at 6 mg/kg body weight. Control (no treatment) or single treatment animals were injected with vehicle (PBS) or implanted with sham pumps depending on the treatment group. All animals experienced a significant decrease in fractional tumor volume when pre-treated with Ro23-7553 before cisplatin as compared to treatment with either agent alone (p<0.001 ANOVA). When tumor regrowth delay (mean±SD of the difference in time for treated and control tumors to reach 4× pretreatment size) was examined, a significant increase was observed in animals treated with Ro23-7553 plus cisplatin as compared either to cisplatin or Ro23-7553 alone (see Table 1)

TABLE 1

| Effect of Ro23-7553 and Cisplatin on Tumor Regrowth Delay | |
|---|---|
| Treatment | Tumor Regrowth Delay |
| Ro23-7553 | 1.8 ± 0.8 |
| Cisplatin | 4.4 ± 0.3 |
| Ro23-7553/cisplatin | 7.7 ± 0.4 |

Example 5

This example demonstrates the potential for sensitizing tumor cells to the effects of cisplatin therapy by pretreatment with a vitamin D derivative and dexamethasone.

SCC cells were incubated with dexamaethasone, 1,25D$_3$, and/or cisplatin, and cell viability was determined via trypan blue exclusion. It was observed that pretreatment with dexamaethasone and 1,25D₃ followed by cisplatin resulted in greater growth inhibition than treatment with any agent alone or pretreatment with 1,25D₃ followed by cisplatin. These results demonstrate that pretreatment with a vitamin D derivative and dexamethasone enhances the antitumor effect of cisplatin.

Example 6

This example demonstrates the potential for sensitizing tumor cells to the effects of cisplatin therapy by pretreatment with a vitamin D derivative and dexamethasone in vivo.

SC tumor-bearing mice were treated with dexamethasone on days 0–3, 1,25D₃ on days 1–3, and/or cisplatin on day 3. Greater antiproliferative activity was observed for the triply-treated animals than for animals treated with dexamethasone followed by cisplatin ($p<0.003$ using the Mann-Whitley test) or with 1,25D₃ followed by cisplatin ($p<0.05$ using the Mann-Whitley test). These results demonstrate that pretreatment with a vitamin D derivative and dexamethasone enhances the antitumor effect of cisplatin.

Example 7

This example demonstrates that vitamin D derivatives can up-regulate a MAPK phosphatase.

SCC cells were treated in vitro with 10 nM 1,25D₃, and untreated cells served as a control. The level of phosphorylated MAPK was assessed at 24 and 48 hours post treatment. Using Western Blot analysis, the amounts of MAPK, MEK (the kinase responsible for phosphorylating MAPK), MKP-1 (a MAPK-specific phosphatase), and growth factor receptors (EGF, PDGF, and IGF1 growth factor receptors) were assessed as well. Additionally, the activity level of MEK was assessed by quantitative in vitro kinase assays.

Cells treated with 1,25D₃ had less phosphorylated MAPK than untreated cells, but the amount of MAPK protein was not affected. The treated cells had slightly less MEK protein present, but the MEK activity profile was not significantly different from the untreated cells. Additionally, the treated cells had significantly higher amounts of EGF, PDGF, and IGF1 growth factor receptors than untreated cells, as well as higher amounts of MKP-1.

The results indicate that 1,25D₃ does not inhibit MAPK by inhibiting the upstream mitogenic signal from growth factor receptors, but that it may inhibit this protein by up-regulating MKP-1.

Example 8

This example demonstrates the potential for sensitizing tumor cells to the effects of conventional cytotoxic carboplatin therapy by pretreatment with a vitamin D derivative.

Carboplatin and 1,25D₃ were tested alone and in combination using the in vitro clonogenic assay. It was observed that pretreatment of cells with 2 nM 1,25D₃ for 48 hours significantly enhanced clonogenic cell kill when compared to carboplatin alone or in concurrent administration (i.e., no pretreatment) of carboplatin in combination with 1,25D₃ ($p<0.001$ ANOVA).

Example 9

This example demonstrates the enhancement of in vivo carboplatin-mediated anti-tumor activity by pretreatment with a vitamin D derivative.

The excision clonogenic kill assay was employed wherein SCCVII/SF tumor bearing animals at 14 days post implantation were treated i.p. for 3 days with 0.5 mg/kg body weight/day of 1,25D₃. On the third day animals received varying doses of carboplatin (between 25 mg/kg body weight and 100 mg/kg body weight). After 24 hours, tumors were harvested, dissociated, and plated for a 7 day incubation. It was observed that pretreatment for 3 days with 1,25D₃ before carboplatin resulted in a significant enhancement of clonogenic cell kill when compared to animals treated with carboplatin or 1,25D₃ alone ($p<0.001$ ANOVA). A significant increase in clonogenic tumor cell kill was observed at each carboplatin dose tested.

In a second experiment, the excision clonogenic kill assay was employed wherein the SCCVII/SF tumor bearing animals at 14 days post implantation were treated i.p. for 3 days with 1,25D₃ at varying doses. On the third day, animals received 50 mg/kg body weight/day carboplatin. After 24 hours, tumors were harvested, dissociated, and plated for a 7 day incubation. It was observed that pretreatment with 1,25D₃ before carboplatin resulted in a significant enhancement of clonogenic cell even at the lowest doses of 1,25D₃. A significant increase in clonogenic tumor cell kill was observed at each carboplatin dose tested as compared to carboplatin alone ($p<0.001$ ANOVA). No animals became hypercalcemic at any of the 1,25D₃ doses tested.

Example 10

This example demonstrates the potential for sensitizing tumor cells to the effects of conventional cytotoxic paclitaxel by pretreatment with a vitamin D analog.

Paclitaxel and 1,25D₃ were tested alone and in combination using the in vitro clonogenic assay as described above. It was observed that pretreatment of cells with 1,25D₃ significantly enhanced clonogenic cell kill when compared to 1,25D₃ ($p<0.001$ ANOVA). It was also observed that concurrent administration of 1,25D₃ and paclitaxel did not result in an enhancement of clonogenic cell kill over paclitaxel alone.

Example 11

This example demonstrates the enhancement of paclitaxel-mediated in vivo anti-tumor activity by pretreatment with 1,25D₃.

The excision clonogenic kill assay was employed wherein SCCVII/SF tumor bearing animals at 11 days post implantation were treated i.p. for 3 days with 0.2 μg/day of 1,25D₃. On the third day, animals received varying doses of paclitaxel. After 24 hours, tumors were harvested, dissociated, and plated for a 7 day incubation. It was observed that pretreatment for 3 days with 1,25D₃ before paclitaxel, at all doses, resulted in a significant enhancement of clonogenic cell kill when compared to animals treated with paclitaxel alone ($p<0.001$ ANOVA). A significant increase in clonogenic tumor cell kill also was observed at each paclitaxel dose tested as compared to paclitaxel alone. No animals became hypercalcemic during these treatments.

Example 12

This example demonstrates the enhancement of in vivo paclitaxel-mediated anti-tumor activity by pretreatment with 1,25D₃.

The tumor regrowth assay was employed wherein SCCVII/SF tumor-bearing mice (day 7 post implantation) were treated with 0.2 μg/mouse 1,25D₃ administered continuously for between two and eight days. At the end of 1,25D₃ administration, paclitaxel was injected i.p. at 40 mg/kg body weight. Control (no treatment) or single treatment animals were injected with vehicle (PBS) or implanted with sham pumps depending on the treatment group. All animals experienced a significant decrease in fractional tumor volume when pre-treated with $1,25D_3$ before paclitaxel as compared to treatment with either agent alone (p<0.00 1 ANOVA).

Example 13

This is an example of a clinical dosing schedule for treatment with carboplatin and $1,25D_3$ in accordance with the inventive method.

Patients with malignant tumors were subject to a treatment regimen involving carboplatin and $1,25D_3$, but 48 hours prior to treatment, each patient was placed on a low calcium diet (250–300 mg/48 hr) and maintained on that diet for at least 7 days. The treatment schedule for the patients is as indicated in Table 2.

TABLE 2

| Cycle | Dosage $1,25D_3$ | Dosage carboplatin |
|---|---|---|
| 1 | 4 μg, SQ, QD 1–3 | AUC 5X1 |
| 2 | 6 μg, SQ, QD 1–3 | AUC 5X1 |
| 3 | 8 μg, SQ, QD 1–3 | AUC 5X1 |
| 4 | 11 μg, SQ, QD 1–3 | AUC 5X1 |
| 5 | 14 μg, SQ, QD 1–3 | AUC 5X1 |
| 6 | 18 μg, SQ, QD 1–3 | AUC 5X1 |
| 7 | 23 μg, SQ, QD 1–3 | AUC 5X1 |
| 8 | 30 μg, SQ, QD 1–3 | AUC 5X1 |
| 9 | 39 μg, SQ, QD 1–3 | AUC 5X1 |

According to this regimen, each cycle lasts four weeks. For successive cycles, the dosage of $1,25D_3$ is increased by 30%. For the first two cycles, the patients were divided into two groups as follows:

Group 1. On day 1, this group of patients was given carboplatin (intravenously as a 30-minute infusion in 100 ml of carrier) at a dose calculated to achieve AUC=5. 24 hours later, a plasma sample was taken to determine carboplatin AUC, and the patients were placed on a three-day regimen of subcutaneous $1,25D_3$ per the schedule indicated in Table 2.

Group 2. On day 1, this group of patients was placed on a three-day regimen of subcutaneous $1,25D_3$. On day 3, the patients were given carboplatin at a dose calculated to achieve AUC=5. 24 hours later, a plasma sample was taken to determine carboplatin AUC.

Following the first cycle, the groups switched between pretreatment and post treatment. For the third and subsequent cycles in this treatment, the patients were placed on a three-day regimen of subcutaneous $1,25D_3$. On day 3, the patients were given carboplatin. at a dose calculated to achieve AUC=5. 24 hours later, a plasma sample was taken to determine carboplatin AUC.

Following the first two cycles, patients were assessed to determine the effect on carboplatin AUC by pretreatment vs. post treatment with $1,25D_3$. The AUC of carboplatin was higher in each patient when pretreated with $1,25D_3$ than when carboplatin was given first (mean AUC=7.8 μg/ml·hr±1.3, carboplatin D1; 6.7 μg/ml·hr±1.3, carboplatin D3). Consistent with the change in AUC, myleosuppression was consistently less in each patient when carboplatin was followed by adjunctive $1,25D_3$.

Example 14

This example demonstrates a method of treating prostate cancer within a patient by adjunctively administrating a vitamin D derivative and dexamethasone to the patient.

Thirty-two patients with androgen-independent prostate cancer were selected on the basis of cancer progression despite anti-androgen withdrawal therapy. The serum prostate-specific antigen (PSA) concentration of each was measured, and they were treated with $1,25D_3$ and dexamethasone on a regimen indicated in Table 3.

TABLE 3

| Cycle | Dosage $1,25D_3$ | Dosage dexamethasone |
|---|---|---|
| 1 (28 days) | 8 μg M-W-F each week | 4 mg Sun (first week) 4 mg M-W-F each week |
| 2 (28 days) | 10 μg M-W-F each week | 4 mg M-W-F each week |
| 3 (28 days) | 12 μg M-W-F each week | 4 mg M-W-F each week |

Patients were evaluated if they completed this regimen, and of the initial 36 patients, 24 were evaluated based on the change in serum PSA levels. Five of the patients exhibited at least a 50% reduction in PSA levels after this treatment, while in the remaining 19 the rate of disease progression was markedly attenuated. No toxicity was observed in any of these patients. These results indicate that co-administration of a vitamin D (or a derivative) and dexamethasone can successfully treat prostate cancer.

Example 15

This example demonstrates that adjunctive administration of zoledronate significantly decreases hypercalcemia mediated by vitamin D-derivatives.

Normal C3H/HeJ mice were pretreated with 10 μg/kg body weight zoledronate and then treated with 0.25 μg $1,25D_3$ once a day for three days. Control animals received $1,25D_3$ alone, and one group of animals received only zoledronate. Following the last $1,25D_3$ treatment, blood was collected at 0, 24 and 48 hours from each mouse, and the serum calcium levels were measured.

Initial calcium levels were significantly reduced in experimental animals as compared to control animals (p=0.00002). 24 and 48 hours later, the serum calcium levels in the control animals remained high (17.2±1.1 mg/dl and 16.5±1.1 mg/dl. respectively), while the serum calcium levels in the experimental animals remained reduced (14.7±0.9 mg/dl and 13.4±0.9 mg/dl, respectively). Additionally, experimental animals, as well as those treated with zoledronate alone, exhibited less dehydration, piloerection, and cachexia attributable to hypercalcemia than did control animals. These results demonstrate that zoledronate significantly decreases hypercalcemia mediated by vitamin D (or a derivative).

Example 16

This is an example of a clinical dosing schedule for treatment with paclitaxel and $1,25D_3$ in accordance with the inventive method.

Patients with malignant tumors were subject to a treatment regimen involving paclitaxel and $1,25D_3$. Paclitaxel was supplied as a sterile solution concentrate (6 mg/ml) in polyethoxylated castor oil 50% and dehydrated ethanol USP 50%. Immediately prior to use, this concentrate was diluted to achieve the appropriate dose in volumes of either 0.9% NaCl injection, USP or 5% dextrose injection, USP (DW5). Preparation was performed in glass to avoid leaching of diethylhexylphthalate plasticizer. $1,25D_3$ was supplied as 0.5 μg tablets from Hoffman-LaRoche Pharmaceutical Corporatoin. The treatment schedule for the patients was as indicated in Table 4.

TABLE 4

| Cycle | Dosage 1,25D$_3$ | Dosage paclitaxel |
|---|---|---|
| 1 | 4 µg orally | 80 mg/m$^2$ IV |
| 2 | 6 µg orally | 80 mg/m$^2$ IV |
| 3 | 8 µg orally | 80 mg/m$^2$ IV |
| 4 | 10 µg orally | 80 mg/m$^2$ IV |
| 5 | 13 µg orally | 80 mg/m$^2$ IV |

According to this regimen, each cycle lasted eight weeks. For successive cycles, the dosage of 1,25D$_3$ was increased by 30%. Within each cycle, 1,25D$_3$ was administered once a day (between 8 am and 12 am) for the first three days. On the third day, 20 mg dexamethasone, 50 mg diphenhydramine, 50 mg rantidine, and antiemetic-ondasteron (10 mg) or ganisteron (1 mg) was administered intravenously 90 minutes following the 1,25D$_3$ administration. Two hours following 1,25D$_3$ administration, the paclitaxel was administered intravenously in 250 ml neutral saline over one hour. Following four days of rest (days 4–7), the three-day treatment, four-day rest routine was repeated until the last day of paclitaxel administration (day 45). The patients then rested for the remainder of the cycle (days 46–63), following which the next cycle was begun.

Incorporation by Reference

All sources (e.g., patent applications, patents, printed publications, and the like) referred to or cited anywhere in this document are hereby incorporated into and made part of this specification by such reference thereto.

Guide to Interpretation

The foregoing is an integrated description of the invention as a whole, not merely of any particular element of facet thereof. The description describes "preferred embodiments" of this invention, including the best mode known to the inventors for carrying it out. Of course, upon reading the foregoing description, variations of those preferred embodiments will become obvious to those of ordinary skill in the art. The inventors expect skilled artisans to employ such variations as appropriate, andthe inventors intend for the invention to be practiced otherwise than as specifically described herein. Accordingly, this invention includes all modifications and equivalents of the subject matter recited in the claims appended hereto as permitted by applicable law.

As used in the foregoing description and in the following claims, singular indicators (e.g., "a" or "one") include the plural, unless otherwise indicated. Recitation of a range of discontinuous values is intended to serve as a shorthand method of referring individually to each separate value falling within the range, and each separate value is incorporated into the specification as if it were individually listed.

As regards the claims in particular, the term "consisting essentially of" indicates that unlisted ingredients or steps that do not materially affect the basic and novel properties of the invention can be employed in addition to the specifically recited ingredients or steps. In contrast, the terms "comprising" or "having" indicate that any ingredients or steps can be present in addition to those recited. The term "consisting of" indicates that only the recited ingredients or steps are present, but does not foreclose the possibility that equivalents of the ingredients or steps can substitute for those specifically recited.

What is claimed is:

1. A method of killing a neoplastic cell within a patient comprising the steps of (a) first administering to a neoplastic cell within the patient a vitamin D derivative and (b) subsequently administering at least one cytotoxic agent to the cell, wherein the cell is susceptible to said steps (a) and (b), and wherein the cytotoxic agent is carboplatin, cisplatin, paclitaxel, or docetaxel.

2. The method of claim 1, wherein step (a) further comprises the administration of a glucocorticoid concurrently with the vitamin D derivative.

3. The method of claim 1, wherein the vitamin D derivative is administered from 1 to 3 days before the cytotoxic agent.

4. The method of claim 1, wherein the vitamin D derivative is administered at least once daily for at least two successive days.

5. The method of claim 1, wherein the vitamin D derivative is administered at least once daily on alternative days.

6. The method of claim 1, wherein the vitamin D derivative is a nonhypercalcemic analog of 1,25D$_3$.

7. The method of claim 6, wherein the analog is Ro23-7553 or Ro24-5531.

8. The method of claim 1, wherein the vitamin D derivative is 1,25D$_3$.

9. The method of claim 8, wherein the patient is human and the daily dose of the vitamin D derivative is between about 4 µg and about 15 µg.

10. The method of claim 9, wherein the daily dose of the vitamin D derivative is between about 8 mg and about 12 mg.

11. The method of claim 1, wherein the cytotoxic agent selectively acts on cells in the G0-G1 phase of the cell cycle.

12. The method of claim 2, wherein the glucocorticoid is dexamethasone.

13. The method of claim 1, wherein the cytotoxic agent is carboplatin and is administered at a dose calculated to achieve AUC of about 5.

14. The method of claim 2, wherein the patient is human and the glucocorticoid is dexamethasone and is administered at a dosing schedule of between about 1 mg and 10 mg on alternative days.

15. The method of claim 1, wherein the cytotoxic agent is paclitaxel and is administered at a dose of about 80 mg/m$^2$.

16. The method of claim 1, further comprising adjunctively administering at least one bisphosphonate selected from the group of bisphosphonates consisting of alendronate, clodronate, etidronate, ibandronate, pamidronate, risedronate, tiludronate, and zoledronate.

17. A method of retarding the growth of a neoplastic tumor within a patient comprising the steps of (a) first administering to the tumor within the patient vitamin D derivative and (b) subsequently administering to the tumor at least one cytotoxic agent, wherein the tumor is susceptible to said steps (a) and (b), and wherein the cytotoxic agent is carboplatin, cisplatin, paclitaxel, or docetaxel.

18. The method of claim 17, wherein step (a) further comprises the administration of a glucocorticoid concurrently with the vitamin D derivative.

19. The method of claim 17, wherein the vitamin D derivative is administered from 1 to 3 days before the cytotoxic agent.

20. The method of claim 17, wherein the vitamin D derivative is administered at least once daily for at least two successive days.

21. The method of claim 17, wherein the vitamin D derivative is administered at least once daily on alternative days.

22. The method of claim 17, wherein the vitamin D derivative is a nonhypercalcemic analog of 1,25D$_3$.

23. The method of claim 22, wherein the analog is Ro23-7553 or Ro24-5531.

24. The method of claim 17, wherein the vitamin D derivative is 1,25$D_3$.

25. The method of claim 24, wherein the patient is human and the daily dose of vitamin D derivative is between about 4 mg 4 mg and about 15 mg.

26. The method of claim 25, wherein the daily dose of the vitamin D derivative is between about 8 mg and about 12 mg.

27. The method of claim 17, wherein the cytotoxic agent selectively acts on cells in the G0-G1 phase of the cell cycle.

28. The method of claim 18, wherein the glucocorticoid is dexamethasone.

29. The method of claim 17, wherein the cytotoxic agent is carboplatin and is administered at a dose calculated to achieve AUC of about 5.

30. The method of claim 18, wherein the patient is human and the glucocorticoid is dexamethasone and is administered at a dosing schedule of between about 1 mg and 10 mg on alternative days.

31. The method of claim 17, wherein the cytotoxic agent is paclitaxel and is administered at a dose of about 80 mg/$m^2$.

32. The method of claim 17, further comprising adjunctively administering at least one bisphosphonate selected from the group of bisphosphonates consisting of alendronate, clodronate, etidronate, ibandronate, pamidronate, risedronate, tiludronate, and zoledronate.

33. The method of claim 1, wherein said cytotoxic agent is docetaxel.

34. The method of claim 17, wherein said cytotoxic agent is docetaxel.

35. The method of claim 1, wherein said vitamin D derivative is 1,25$D_3$ and wherein said cytotoxic agent is docetaxel.

36. The method of claim 17, wherein said vitamin D derivative is 1,25$D_3$ and wherein said cytotoxic agent is docetaxel.

* * * * *

UNITED STATES PATENT AND TRADEMARK OFFICE
CERTIFICATE OF CORRECTION

PATENT NO. : 6,559,139 B1
DATED : May 6, 2003
INVENTOR(S) : Candace S. Johnson and Donald L. Trump It is certified that error appears in the above-identified patent and that said Letters Patent is hereby corrected as shown below:

Column 3,
Line 26, the word "pf" should read -- of --.

Column 4,
Line 16, the comma "," after the word "or" should be deleted.

Column 6,
Line 8, "invention: as" should read -- invention; as --.

Column 7,
Line 53, "bisphosphonatescan" should read -- bisphosphonates can --.

Column 8,
Line 35, "in vitro" should be italicized.

Column 10,
Line 31, "in vivo" should be italicized.
Line 32, "displatin-mediated" should read -- cisplatin-mediated --.
Line 66, "dexamathaesone" should read -- dexamathasone --.

Column 11,
Line 2, "dexamathaesone" should read -- dexamathasone --.
Line 12, "in vivo" should be italicized.

Column 13,
Line 7, "(p>0.00 1 ANOVA)" should read -- (p>0.001 ANOVA) --.
Line 51, the period (".") after "carboplatin" should be deleted.

Column 14,
Lines 65-66, the word "Corporatoin" should read -- Corporation --.

Column 15,
Line 42, "andthe" should read -- and the --.

Column 16,
Lines 27-28, "8 mg" and "12 mg" should read -- 8 $\mu$g -- and -- 12 $\mu$g -- respectively.
Line 30, "G0-G1" should read -- $G_0$-$G_1$ --.
Line 49, the word -- a -- should be inserted between the words "patient" and "vitamin".

UNITED STATES PATENT AND TRADEMARK OFFICE
CERTIFICATE OF CORRECTION

PATENT NO.   : 6,559,139 B1
DATED        : May 6, 2003
INVENTOR(S)  : Candace S. Johnson and Donald L. Trump It is certified that error appears in the above-identified patent and that said Letters Patent is hereby corrected as shown below:

Column 17,
Line 6, the word -- the -- should be inserted between the words "of" and "vitamin".
Line 7, the second occurrence of "4 mg" should be deleted, and "4 mg" and "15 mg" should read -- 4 $\mu$g -- and -- 15 $\mu$g -- respectively.
Lines 9-10, "8 mg" and "12 mg" should read -- 8 $\mu$g -- and -- 12 $\mu$g -- respectively.
Line 12, "G0-G1" should read -- $G_0$-$G_1$ --.

Signed and Sealed this

Twenty-third Day of March, 2004

JON W. DUDAS
*Acting Director of the United States Patent and Trademark Office*